United States Patent [19]
Taheri

[11] Patent Number: 4,624,244
[45] Date of Patent: Nov. 25, 1986

[54] DEVICE FOR AIDING CARDIOCEPITAL VENOUS FLOW FROM THE FOOT AND LEG OF A PATIENT

[76] Inventor: Syde A. Taheri, 268 Dan Troy, Williamsville, N.Y. 14221

[21] Appl. No.: 692,579

[22] Filed: Jan. 18, 1985

Related U.S. Application Data

[63] Continuation-in-part of Ser. No. 660,802, Oct. 15, 1984, abandoned.

[51] Int. Cl.⁴ ........................ A61H 23/04; A61M 1/00
[52] U.S. Cl. .................................... 128/24 R; 128/38; 128/DIG. 15
[58] Field of Search ............... 128/24 R, DIG. 15, 38, 128/25 R

[56] References Cited

U.S. PATENT DOCUMENTS

| | | | |
|---|---|---|---|
| 1,608,239 | 11/1926 | Rosett | 128/44 |
| 3,454,010 | 7/1969 | Lilligren | 128/24 R |
| 3,659,593 | 5/1972 | Vail | 128/DIG. 15 |
| 3,683,897 | 8/1972 | Shield | 128/25 R |
| 3,862,629 | 1/1975 | Rotta | 128/24 R |
| 3,933,150 | 1/1976 | Kaplan | 128/DIG. 15 |
| 4,044,759 | 8/1977 | Ghayouran | 128/24 R |
| 4,338,923 | 7/1982 | Gelfer | 128/24 R |

FOREIGN PATENT DOCUMENTS

| | | | |
|---|---|---|---|
| 837750 | 5/1952 | Fed. Rep. of Germany | 128/24 R |
| 1175948 | 11/1958 | France | 128/24 R |
| 654255 | 3/1979 | U.S.S.R. | 128/24 R |
| 848028 | 7/1981 | U.S.S.R. | 128/24 R |

*Primary Examiner*—Clyde I. Coughenour
*Attorney, Agent, or Firm*—Joseph P. Gastel

[57] ABSTRACT

A device for aiding cardiocepital venous flow from the foot and leg of a patient including a first flexible fabric cuff for encircling the arch and instep of a patient's foot, a first bladder in the first cuff for placement in contiguous relationship to the arch, a second cuff for encircling the leg of the patient, a plurality of sequentially ascending second bladders in the second cuff for placement in contiguous relationship to the calf of the leg of the patient, a first conduit in communication with the first bladder, and second conduits in communication with the second bladders. A modification includes cuff structure for encircling the toes of the patient.

16 Claims, 12 Drawing Figures

TO BLADDER A
TO BLADDER B
TO BLADDER C
TO BLADDER D
53
55
57
60
27
32
61
13
35
62
35
D
59
51
43
34
63
34
39
47
46
70
50
C
42
56
37
45
33
64
33
49
B
36
41
44
10
15
53
11
54
16
A
21
24
22
25
23
20
19
26
48
C
48
14
13
27

40
45
37
47

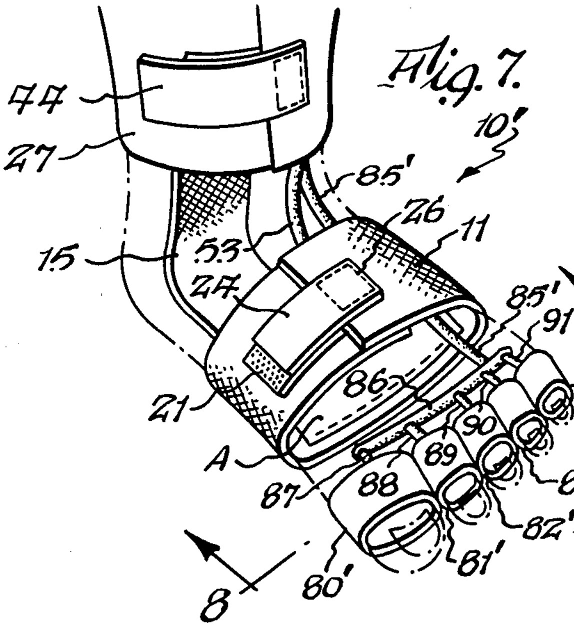
Fig. 7.
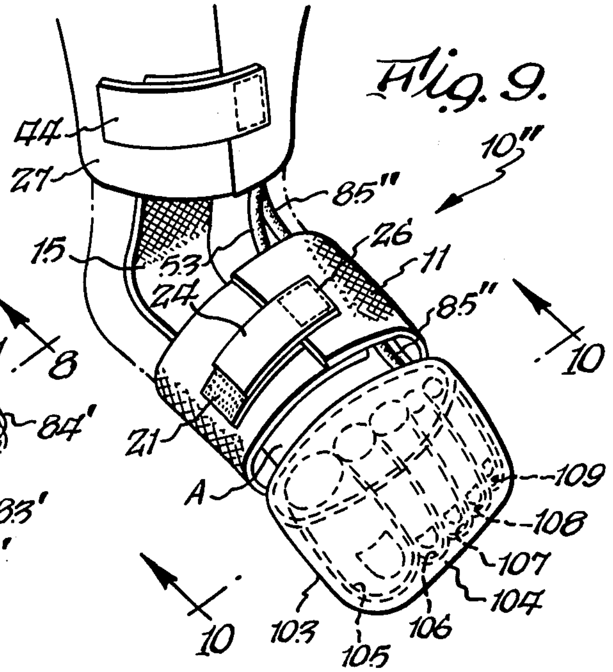
Fig. 9.
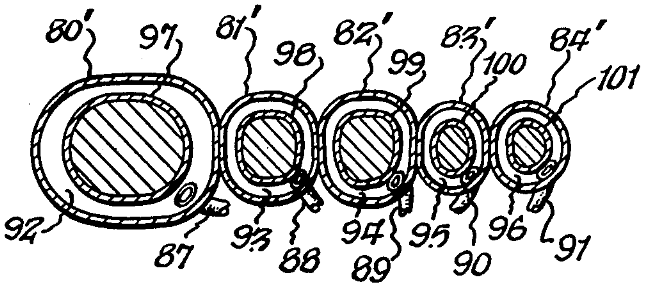
Fig. 8.
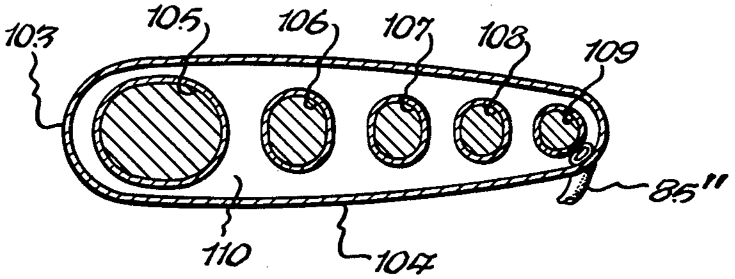
Fig. 10.
Fig. 11.
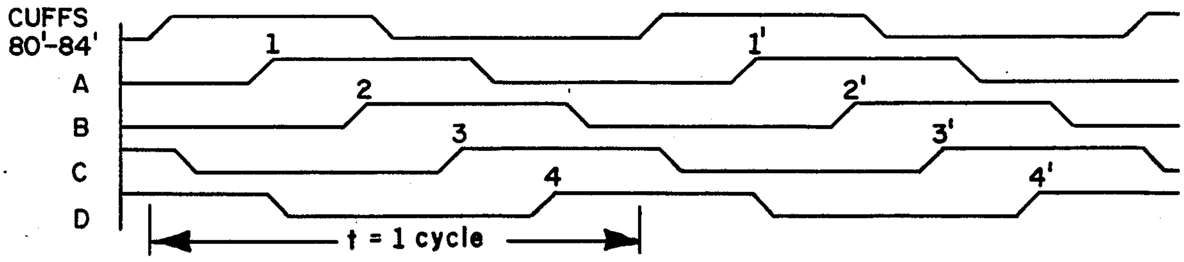

DEVICE FOR AIDING CARDIOCEPITAL VENOUS FLOW FROM THE FOOT AND LEG OF A PATIENT

CROSS REFERENCE TO RELATED APPLICATION

The present application is a continuation-in-part of application Ser. No. 660,802, filed Oct. 15, 1984 now abandoned.

BACKGROUND OF THE INVENTION

The present invention relates to an improved device for aiding cardiocepital venous flow from the foot and leg of a patient who may be suffering from diseased leg veins which results in venous hypertension.

In the past, numerous devices have been disclosed for aiding cardiocepital venous flow to prevent venous hypertension. These devices usually included boots placed around the foot and leg and pressure was applied to the foot and leg. However, the prior devices were extremely cumbersome and usually required the patient to remain immobile. In addition, the prior devices did not concentrate the pressure in those areas in which it was most effective, namely, the soft tissue areas of the foot and leg, and therefore they did not operate efficiently.

SUMMARY OF THE INVENTION

It is accordingly one object of the present invention to provide an improved device for aiding cardiocepital venous flow which applies pressure to the soft flesh areas of the foot and leg to thereby provide a highly efficient pressure distribution which aids blood flow in the deep veins.

Another object of the present invention is to provide an improved device for aiding cardiocepital deep vein flow which is portable and lightweight and which can be worn by an ambulatory patient. Other objects and attendant advantages of the present invention will readily be perceived hereafter.

The present invention relates to a device for aiding cardiocepital venous flow from the foot and leg comprising a first cuff for encircling the arch and instep of said foot, a first bladder in said first cuff for placement in contiguous relationship to said arch, a second cuff for encircling said leg, a plurality of sequentially ascending second bladders in said second cuff for placement in contiguous relationship to the calf of said leg, first conduit means in communication with said first bladder, and second conduit means in communication with said second bladders. A modification includes cuff structure for encircling the toes of the patient.

The various aspects of the present invention will be more fully understood when the following portions of the specification are read in conjunction with the accompanying drawings wherein:

BRIEF DESCRIPTION OF THE DRAWINGS

FIG. 7 is a fragmentary perspective view of a modified form of the present invention which includes cuffs encircling the toes;

FIG. 8 is a fragmentary cross sectional view taken substantially along line 8—8 of FIG. 7;

FIG. 9 is a fragmentary perspective view of another embodiment of the present invention which includes an inflatable pocket for receiving the toes; and FIG. 10 is a fragmentary perspective view taken substantially along line 10—10 of FIG. 9; and FIG. 11 is a graph depicting the sequence of inflation of an embodiment which incorporates the cuffs of FIGS. 7 or 9 and which operates in a cycle analogous to FIG. 5.

DESCRIPTION OF THE PREFERRED EMBODIMENTS

Figures 1, 2:
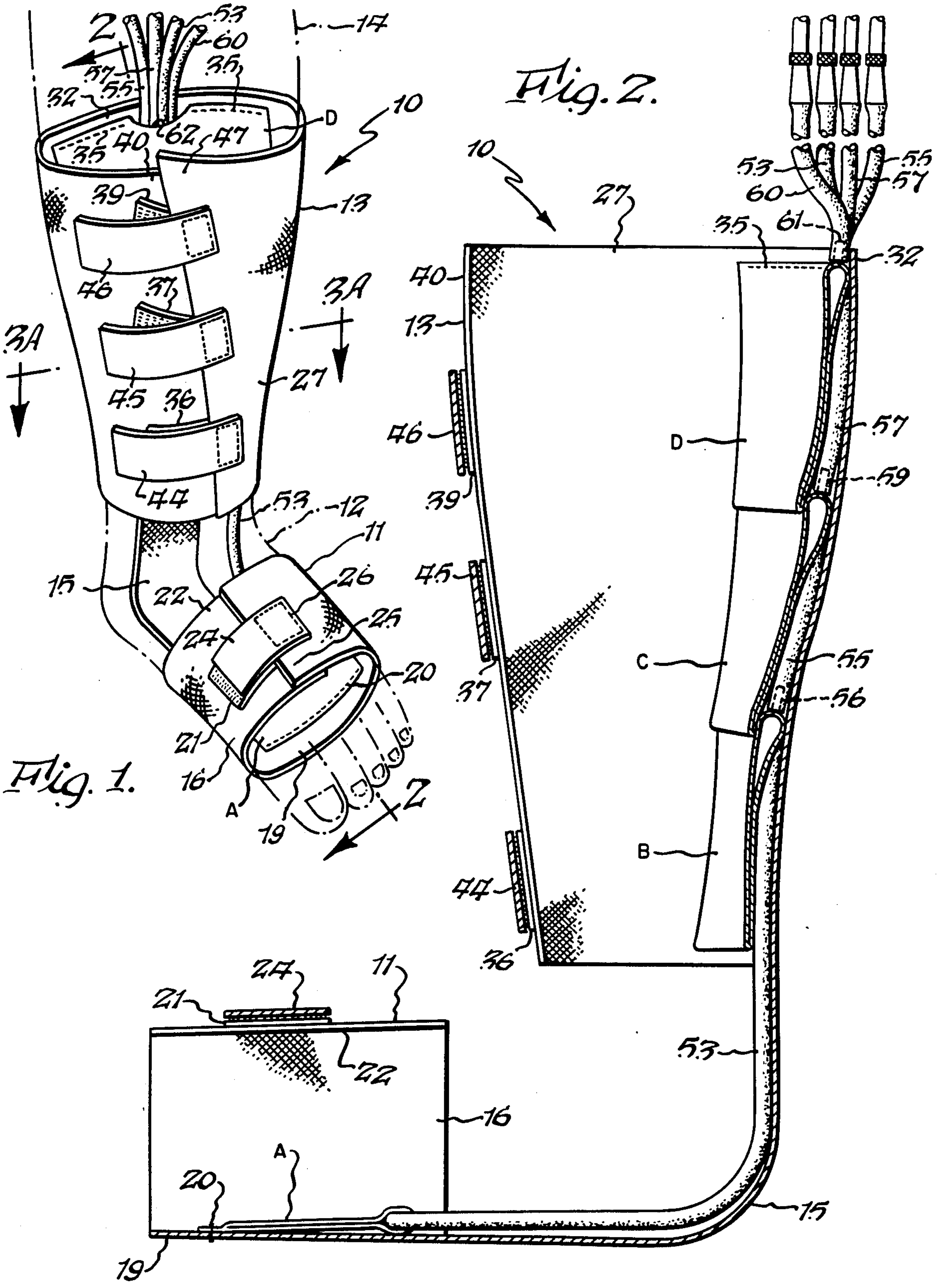
FIG. 1 is a perspective view of the improved device of the present invention shown in encircling engagement with the foot and leg of a patient, which are shown in phantom.
FIG. 2 is a fragmentary cross sectional view taken substantially along line 2—2 of FIG. 1 with the foot and leg omitted.

The improved device 10 for aiding cardiocepital deep vein flow from the foot and leg includes a first cuff 11 for encircling the arch and instep of a patient's foot 12, and it also includes a second cuff 13 for encircling the leg 14 of a patient. The first cuff 11 is confined substantially to the area about the arch and the second cuff 13 extends from approximately above the ankle to just below the knee. A strap-like member 15 connects cuff 11 to cuff 13.

In its more specific aspects, cuff 11 comprises a flexible substantially planar fabric member 16 which is substantially rectangular in plan. A bladder A is sewn to the central portion 19 of member 16 by a row of stitching 20. A tab 21 of pile fabric is sewn to the outer edge portion 22 of member 16 by stitching 23 and a tab 24 of hook fabric is sewn to the outer edge portion 25 of member 16 by stitching 26. Tabs 21 and 24 comprise a hook and pile type of fastener which is generally known under the trademark VELCRO. Member 16 is a very thin, light fabric, such as nylon cloth.

Figures 3, 3A:
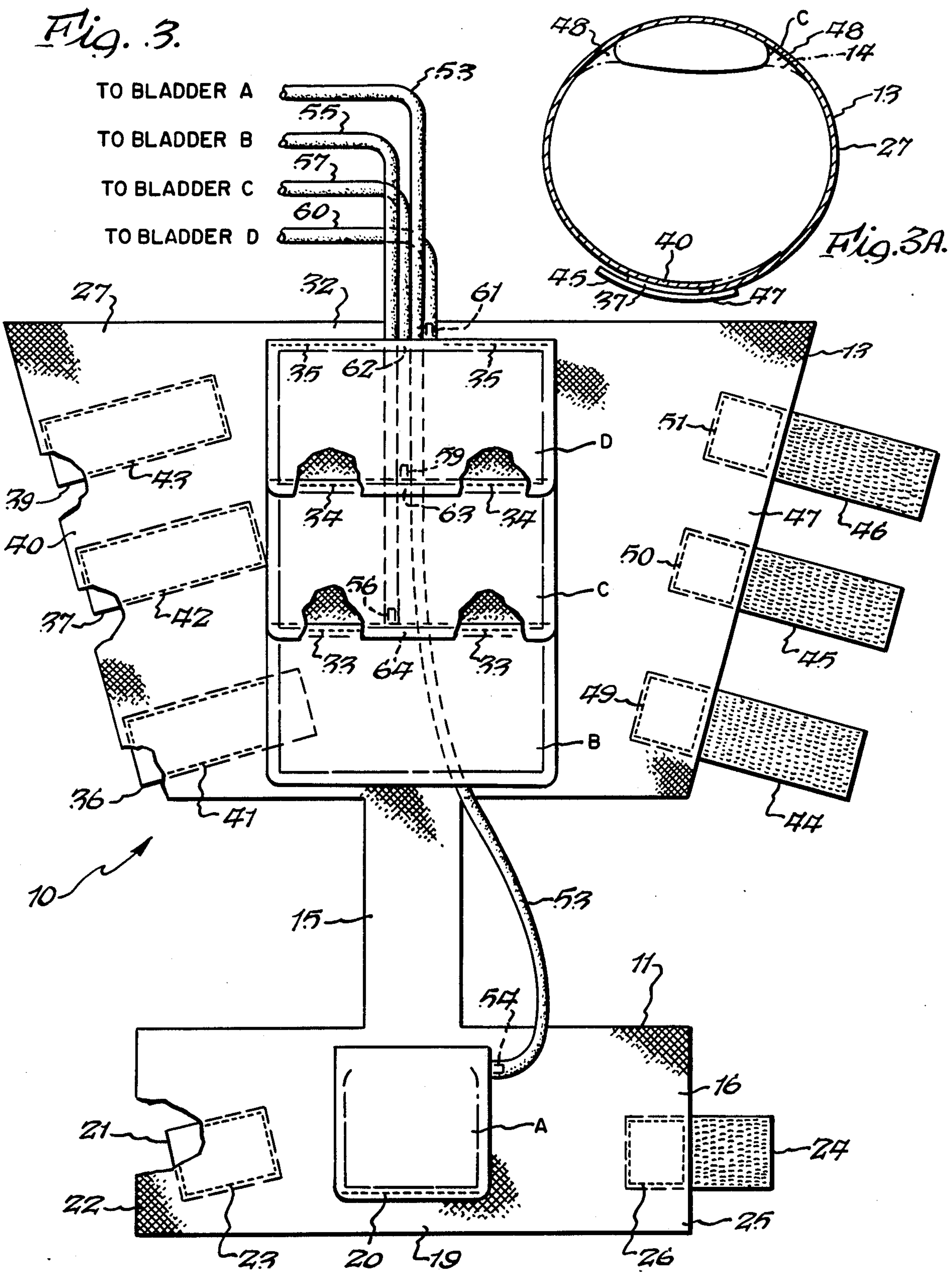
FIG. 3 is a fragmentary plan view, with portions broken away, showing the device in a fully open condition.
FIG. 3A is a schematic cross-sectional view taken substantially along line 3A—3A of FIG. 1.

Cuff 13 comprises a flexible substantially planar member 27 in the shape of a regular trapezoid in plan, and it is formed from the same type of cloth as cuff 11. Bladders B, C and D are sewn to central portion 32 of member 27 by rows of stitching 33, 34 and 35, respectively, and they are in end-to-end relationship. Pile tabs 36, 37 and 39 are sewn to outer edge portion 40 of member 27 by stitching 41, 42 and 43, respectively. Tabs 44, 45 and 46 of hook fabric are sewn to outer edge portion 47 by stitching 49, 50 and 51, respectively. Tabs 36, 37, and 39 and 44-46 are generically known as hook and pile fasteners which are identified under the trademark VELCRO. Strap 15 is formed integrally with members 16 and 27. Bladders A, B, C and D do not extend more than about one-half the width of their respective cuffs so as to confine them substantially to the area of the soft tissue proximate the deep veins which they are to press against. When the bladders are inflated, there are spaces 48 outside of the outer side edges of the bladders where the cuffs do not press against the flesh, as schematically shown in FIG. 3A, thus never cutting off circulation completely in rings around the leg or arch.

As will be explained more fully hereafter, bladders A, B, C and D are sequentially inflated by compressed air and are sequentially deflated. To effect inflation of the bladders, a conduit 53 is mounted on nipple 54 which is in communication with bladder A; a conduit 55 is mounted on nipple 56 on bladder B; a conduit 57 is mounted on nipple 59 of bladder C; and a conduit 60 is mounted on nipple 61 of bladder D. The conduits 53, 55, 57 and 60 are-positioned between member 27 and bladders B, C and D, as shown in FIG. 3, by passing through gap 62 in row of stitching 35, gap 63 in row of stitching 34, and gap 64 in row of stitching 33.

In use the cuff 11 is placed in encircling engagement with foot 12 with the bladder A against the soft tissue of the arch, and cuff 13 is placed in encircling engagement with the leg with bladders B, C and D against the soft tissue of the calf. The various fasteners are secured so that the cuffs 11 and 13 fit snugly, but not so tight as to impair circulation. As can be visualized, the fasteners are adjustable so that the device will properly fit legs of different shapes and sizes. When the bladders are inflated, they will bulge inwardly toward the adjacent soft tissue to provide good pressure against the deep veins. In the installed position, strap 15 lies under and passes around the back of the heel of the foot, as shown in FIGS. 1 and 2.

Figure 4:
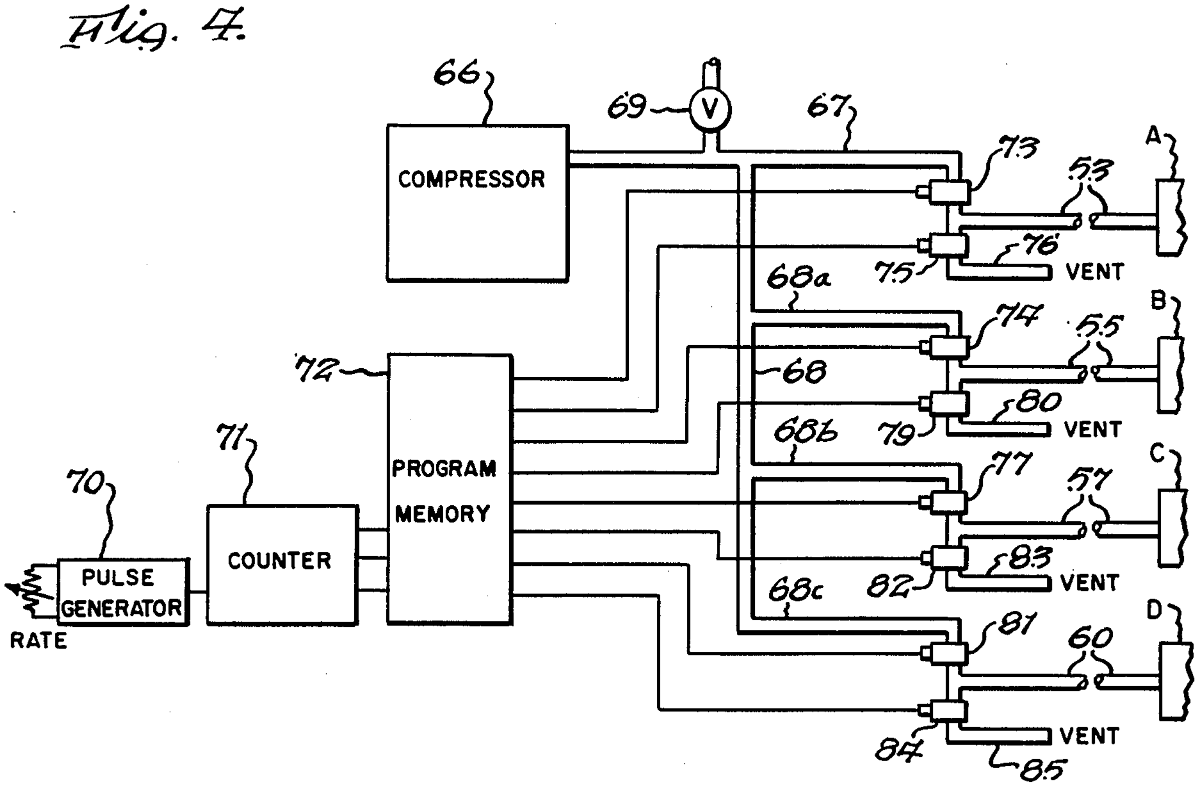
FIG. 4 is a fragmentary schematic view of the control for the device and also showing the associated pneumatic circuits.

In FIG. 4 the controls and pneumatic circuit are shown. A compressor 66 supplies compressed air to conduits **67, 68, 68*a*, 68*b* and 68*c* having relief valve 69 in communication therewith. A pulse generator 70 is provided coupled to a counter 71 which in turn is coupled to a program memory 72. The foregoing electronic components sequentially actuate various normally closed solenoid valves as follows. To inflate bladder A through conduits 67 and 53, solenoid valve 73 is opened and it remains open for the period shown by numeral 1 in FIG. 5. The inflation of bladder A will compress the vein in the soft tissue area of the arch to force venous blood cardiocepitally. Approximately midway during the inflation cycle 1 of bladder A and while solenoid 73 is open, solenoid valve 74 is opened at time 2 to inflate bladder B through conduits 68, 68*a* and 55 to compress the portions of the vein near the ankle and thus aid in carrying blood upwardly. Approximately midway during the inflation cycle of bladder B, solenoid valve 73 is closed, and venting solenoid valve 75 is opened to vent bladder A through conduits 53 and 76. However, substantially simultaneously at time 3, bladder C is inflated through conduits 68, 68*b* and 57 by opening solenoid valve 77. Approximately midway during the inflation cycle of bladder C, bladder B is deflated by closing solenoid valve 74 and opening venting solenoid valve 79 to permit bladder B to be vented through conduits 55 and 80. Thus, the inflation of bladder C will also force venous blood cardiocepitally. Approximately midway during the inflation cycle of bladder C, bladder D is inflated through conduits 68, 68*c* and 60 at time 4 by opening solenoid valve 81. Approximately midway during the inflation cycle of bladder D, bladder C is deflated by closing solenoid valve 77 and opening solenoid valve 82 to permit bladder C to be vented through conduits 57 and 83. Thus, the inflation of bladder D will further move venous blood cardiocepitally. Proximate the end of the inflation cycle of bladder D, bladder A is again inflated by opening solenoid valve 73. Shortly after bladder A is inflated, bladder D is deflated by closing solenoid valve 81 and opening solenoid valve 84 to permit bladder D to be vented through conduits 60 and 85. The foregoing cycles are then repeated as shown by the succeeding numerals 1′, 2′, 3′ and 4′**.

Figure 5:
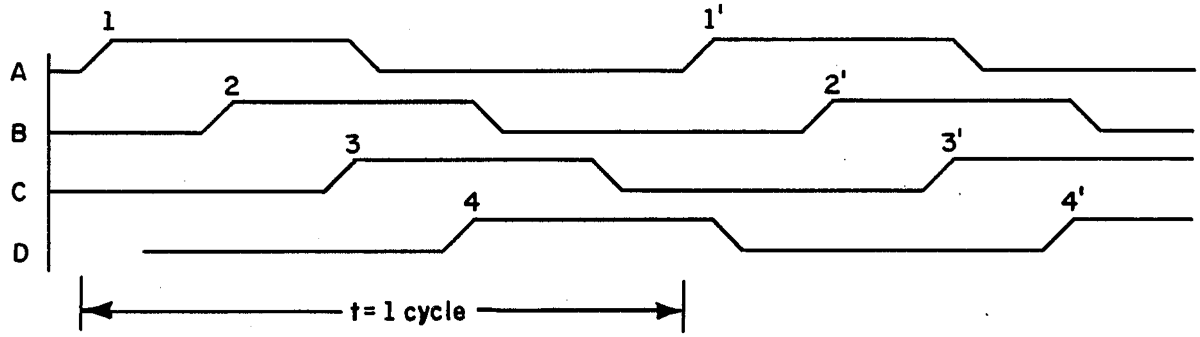
FIG. 5 is a graph depicting one sequence of inflation of the various bladders.
Figure 6:
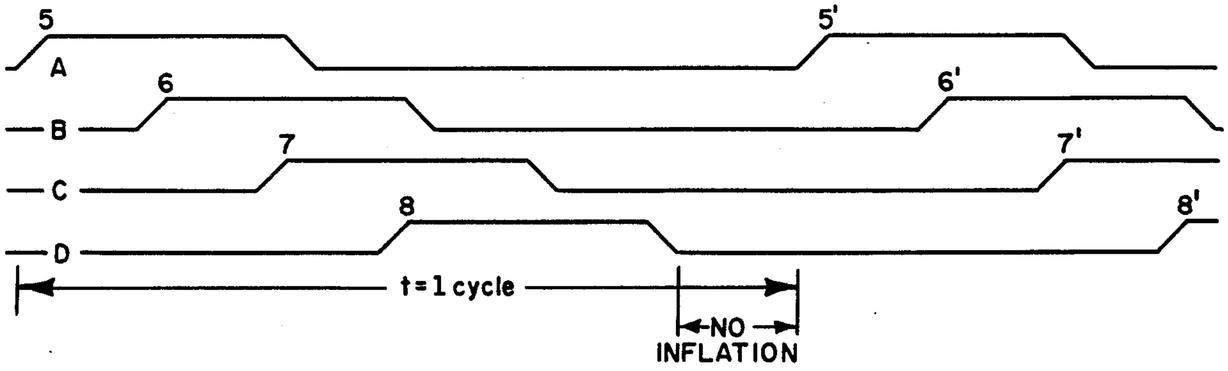
FIG. 6 is a graph depicting another series of inflation of the bladders.

As can be seen from the graph of FIG. 5, there is an overlap between the inflation of bladders A and D. However, for certain patients it may be desirable to have a gap between the deflation of bladder D and the subsequent inflation of bladder A. This cycle is shown in FIG. 6 wherein the inflation time for bladders A, B, C and D are shown by numerals 5, 6, 7 and 8, respectively, and subsequently by numerals 5′, 6′, 7′ and 8′, respectively, with a gap of no inflation between 8 and 5′.

In use the length of time of the inflation cycle was approximately fifteen seconds, and the air pressure in a fully inflated bladder was between about 90 and 100 mm of mercury. Bladder A measured about 3 inches square, and bladders B, C and D measured approximately 6 inches by 3 inches. Cuff 11 when opened flat, as shown in FIG. 3, measured 12 inches by $4\frac{1}{2}$ inches. Cuff 13 had a small base of about $11\frac{1}{2}$ inches, a large base of about 18 inches, and a height of about 10 inches. Strap 15 measured $5\frac{1}{2}$ inches by 2 inches.

In an actual test, the device of the present invention reduced a patient's venous leg pressure from 64 mm of mercury to 42 mm, as compared to a device without the foot cuff which only reduced it from 62 mm to 58 mm. The prior device used bladders which encircled the entire leg and did not apply the bladder pressure only to the soft tissue areas of the calf. It is believed that the improved result is due to the removal of venous blood from the foot by the use of bladder A in cuff 11, as it operates in the above-described sequence with bladders B, C and D, and also to the applying of bladder pressure only to the soft tissue areas of the foot and calf.

The compressor 66 is a small portable battery operated pump, and the electronics 70, 71 and 72 consist of a microcircuit which has very small volume and weight. The foregoing features thus enhance the portability of the device.

While the foregoing description has referred to blood flow in the deep veins, it is to be understood that the present device also enhances blood flow in the superficial veins, which are not as important as the deep veins relative to the matter of venous hypertension.

In FIGS. 7 and 8 a modified embodiment 10′ of the present invention is shown. This embodiment includes all of the structure described above relative to FIGS. 1–6, and like numerals will denote like parts. However, this modification also includes a plurality of inflatable cuffs 80′, 81′, 82′, 83′ and 84′ for encircling the patient's individual toes as shown. An additional conduit 85′ is in communication with conduit 67 (FIG. 4) and passes through gaps 62, 63, and 64 and runs next to the portion of conduit 53 between cuffs 13 and 11. Conduit 85′ passes next to bladder A and leads to manifold 86, which is located beneath the toes but can be located in any other desired area. Manifold 86 has conduits 87, 88, 89, 90 and 91 in communication with cuffs 80′, 81′, 82′, 83′ and 84′, respectively.

Cuffs 80′–84′ are inflated simultaneously and they are inflated for the same length of time as each of bladders A, B, C and D, as shown in FIG. 5, except that they are inflated in advance of time 1 (FIG. 5) by the same length of time that bladder A is inflated in advance of bladder B, as shown in FIG. 5. Furthermore, cuffs 80'–84' are maintained in an inflated condition until approximately midway in the inflation cycle of bladder A and then they are vented to the atmosphere. The structure for achieving the foregoing is analogous to solenoids 73 and 75 and the associated conduits of FIG. 4. Thus, the time sequence of FIG. 5 has been expanded to include the inflation of cuffs 80'–84', as can be seen from FIG. 11. Alternatively, if desired, the cuffs 80'–84' can be inflated according to the cycle of FIG. 6, with cuffs 80'–84' being inflated at the beginning of the cycle.

As the chambers 92, 93, 94, 95 and 96 of cuffs 80'–84', respectively, are inflated, the internal resilient walls 97, 98, 99, 100 and 101, respectively, will be forced into pressing engagement with the toes with which they are in contiguous relationship to thereby press the blood out of the toes. The cardiocepitally moving blood is thus forced into the area of the arch whereupon the subsequent inflation of bladder A in cuff 11 will then force the blood toward cuff 27, as described in detail above.

The reason for using cuffs 80'–84' is to prevent blood from being forced into the toes during the inflation of bladder A in cuff 11. While cuffs 80'–84' have been shown as not encircling the portions of the toes on which the toenails are located, it is preferable to make the cuffs 80'–84' as long as possible to thereby force as much blood as possible out of the toes. Furthermore, while cuffs 80'–84' have been shown as annular members, it will be appreciated that they can have the construction of cuff 11 of FIG. 1 wherein bladders are mounted on the inner surface of bands for pressing against the soft tissue of the toes and the bands can have their opposite ends fastened to each other by hook and pile fasteners of the type shown in FIG. 1 and associated with cuff 11.

Another embodiment 10" of the present invention is shown in FIGS. 9 and 10. This embodiment includes all of the structure of FIGS. 1–6 as described above relative to FIGS. 7 and 8. However, this embodiment differs from FIG. 7 in that it utilizes a cuff 103 in the nature of a cup-like member which receives the toes in their entireties. Cup-like member 103 includes an outer casing 104 having flexible resilient pockets 105, 106, 107, 108 and 109 for receiving the toes as shown. All of the pockets 105–109 are located in chamber 110. A conduit 85", which is analogous to conduit 85' of FIG. 7, is in communication with chamber 110 and it periodically supplies compressed air thereto or vents it in the same sequence relative to cuff 11 as described above relative to cuffs 80'–84'. The advantage of the embodiment of FIGS. 9 and 10 is that it provides pressure to all of the soft tissue of all of the toes when the flexible resilient pockets 105–109 are pressed against the toes by air pressure in chamber 110. If desired, the cuffs of FIGS. 7 and 9 may be attached to cuff 11 by straps which are analogous to strap 15 which attaches cuff 11 to cuff 13.

It can thus be seen that the improved devices of the present invention are manifestly capable of achieving the above-enumerated objects, and while preferred embodiments have been disclosed, it will be appreciated that the present invention is not limited thereto but may be otherwise embodied within the scope of the following claims.

What is claimed is:

1. A portable device for aiding cardiocepital venous flow from the foot and leg of an ambulatory patient, said foot including an instep and an arch with soft tissue associated therewith and said leg including a calf with soft tissue associated therewith, said device comprising a first cuff for encircling the arch and instep of said foot, said first cuff comprising a first flexible substantially planar member having a first central portion and first outer edge portions, a first bladder of a size for placement substantially only in contiguous relationship to said soft tissue of said arch, means for securing said first bladder to said first central portion of said first cuff such that portions of said first flexible substantially planar member on opposite sides of said first bladder extend laterally beyond said first bladder with first spaces proximate said opposite sides of said first bladder, said first spaces being located between said portions of said first flexible substantially planar member and said arch to permit circulation in the flesh of said arch proximate said first spaces when said first bladder is inflated, a second cuff for encircling said leg, said second cuff comprising a second flexible substantially planar member having a second central portion and second outer edge portions, a plurality of sequentially ascending second bladders of a size for placement substantially only in contiguous relationship to said soft tissue of said calf for exerting pressure on the deep veins of the leg, means for securing said second bladders to said second central portion of said second cuff such that portions of said second flexible substantially planar member on opposite sides of said second bladder extend laterally beyond said second bladder with second spaces proximate said opposite sides of said second bladder, said second spaces being located between said portions of said second flexible substantially planar member and said leg to permit circulation in the flesh of said leg proximate said second spaces when said second bladders are inflated, first conduit means in communication with said first bladder, second conduit means in communication with said second bladders for effecting sequential inflation of said second bladders, first fastening means on said first outer edge portions for securing said outer edge portions relative to each other when said first cuff is placed in encircling engagement with said foot, and second fastening means on said second outer edge portions for securing said second outer edge portions relative to each other when said second cuff is placed in encircling engagement with said leg.

2. A device as set forth in claim 1 including a strap-like member connecting said first and second cuffs and for extending around the heel of said leg.

3. A device as set forth in claim 1 including first means for adjusting the diameter of said first cuff, and second means for adjusting the diameter of said second cuff.

4. A device as set forth in claim 1 wherein said first fastening means comprise hook and pile fabric.

5. A device as set forth in claim 4 wherein said second fastening means comprise a plurality of hook and pile fasteners extending along said second outer edge portions.

6. A device as set forth in claim 1 including a strap-like member substantially in line with said first and second central portions for connecting said first and second substantially planar members and for extending around the heel of said leg.

7. A device as set forth in claim 1 wherein certain of said second bladders do not extend laterally more than about half the distance between said second outer edge portions.

8. A device as set forth in claim 7 wherein said first bladder does not extend laterally more than about half the distance between said first outer edge portions.

9. a device as set forth in claim 1 wherein said second flexible substantially planar member is trapezoidal in shape with a smaller base proximate said first cuff.

10. A device as set forth in claim 1 wherein said second conduit means comprise a conduit in communication with each of said second bladders.

11. A device a set forth in claim 1 including additional cuff means for encircling the toes of a patient, and third conduit means in communication with said additional cuff means.

12. A device for aiding cardiocepital venous flow from the foot and leg, said foot including an instep and an arch with soft tissue associated therewith and said leg including a calf with soft tissue associated therewith, said device comprising a first cuff for encircling the arch and instep of said foot, said first cuff comprising a flexible substantially planar member having a first central portion and first outer edge portions, a first bladder of a size for placement substantially only in contiguous relationship to said soft tissue of said arch, means for securing said first bladder to said first central portion of said first cuff, a second cuff for encircling said leg, said second cuff comprising a second flexible substantially planar member having a second central portion and second outer edge portions, a plurality of sequentially ascending second bladders of a size for placement substantially only in contiguous relationship to said soft tissue of said calf, means for securing said second bladders to said second central portion of said second cuff, first conduit means in communication with said first bladder, second conduit means in communication with said second bladders, first fastening means on said first outer edge portions for securing said outer edge portions relative to each other when said first cuff is placed in encircling engagement with said foot, second fastening means on said second outer edge portions for securing said second outer edge portions relative to each other when said second cuff is placed in encircling engagement with said leg, additional cuff means for encircling the toes of a patient, and third conduit means in communication with said additional cuff means, said additional cuff means comprising a plurality of individual cuff members for encircling said toes individually.

13. A device for aiding cardiocepital venous flow from the foot and leg, said foot including an instep and an arch with soft tissue associated therewith and said leg including a calf with soft tissue associated therewith, said device comprising a first cuff for encircling the arch and instep of said foot, said first cuff comprising a flexible substantially planar member having a first central portion and first outer edge portions, a first bladder of a size for placement substantially only in contiguous relationship to said soft tissue of said arch, means for securing said first bladder to said first central portion of said first cuff, a second cuff for encircling said leg, said second cuff comprising a second flexible substantially planar member having a second central portion and second outer edge portions, a plurality of sequentially ascending second bladders of a size for placement substantially only in contiguous relationship to said soft tissue of said calf, means for securing said second bladders to said second central portion of said second cuff, first conduit means in communication with said first bladder, second conduit means in communication with said second bladders, first fastening means on said first outer edge portions for securing said outer edge portions relative to each other when said first cuff is placed in encircling engagement with said foot, second fastening means on said second outer edge portions for securing said second outer edge portions relative to each other when said second cuff is placed in encircling engagement with said leg, additional cuff means for encircling the toes of a patient, and third conduit means in communication with said additional cuff means, said additional cuff means comprising a pocket-like member having individual compartments for receiving the toes.

14. A device as set forth in claim 13 wherein said individual compartments are located within a casing, and wherein a chamber within said casing for receiving compressed air from said third conduit means surrounds said compartments.

15. A device for aiding cardioceptial venous flow from the foot and leg, said foot including an instep and an arch with soft tissue associated therewith and said leg including a calf with soft tissue associated therewith, said device comprising a first cuff for encircling the arch and instep of said foot, said first cuff comprising a flexible substantially planar member having a first central portion and first outer edge portions, a first bladder of a size for placement substantially only in contiguous relationship to said soft tissue of said arch, means for securing said first bladder to said first central portion of said first cuff, a second cuff for encircling said leg, said second cuff comprising a second flexible substantially planar member having a second central portion and second outer edge portions, a plurality of sequentially ascending second bladders of a size for placement substantially only in contiguous relationship to said soft tissue of said calf, means for securing said second bladders to said second central portion of said secoud cuff, first conduit means in communication with said first bladder, second conduit means in ccmmunication with said second bladders, first fastening means on said first outer edge portions for securing said outer edge portions relative to each other when said first cuff is placed in ercircling engagement with said foot, second fastening means on said second outer edge portions for securing said second outer edge portions relative to each other when said second cuff is placed in encircling engagement with said leg, each of said bladders including a top edge and a bottom edge, said means for securing said second bladders to said central portion of said second cuff comprising attachment means proximate said top edges, and gaps in said attachment means for receiving said second conduit means and permitting certain of said second conduit means to be located between said second substantially planar member and said second bladders.

16. A device as set forth in claim 15 wherein said gaps also receive said first conduit means and permit said first conduit means to be located between said second substantially planar member and said second bladders.

* * * * *